(12) United States Patent
Batchelder et al.

(10) Patent No.: US 8,515,513 B2
(45) Date of Patent: Aug. 20, 2013

(54) SYSTEM AND METHOD FOR FACILITATING OBSERVATION OF MONITORED PHYSIOLOGIC DATA

(75) Inventors: Keith Batchelder, New York, NY (US); Scott Amundson, Oakland, CA (US); James Ochs, Seattle, WA (US); Paul Mannheimer, Danville, CA (US)

(73) Assignee: Covidien LP, Mansfield, MA (US)

( * ) Notice: Subject to any disclaimer, the term of this patent is extended or adjusted under 35 U.S.C. 154(b) by 964 days.

(21) Appl. No.: 12/609,344

(22) Filed: Oct. 30, 2009

(65) Prior Publication Data

US 2010/0113904 A1   May 6, 2010

Related U.S. Application Data

(60) Provisional application No. 61/111,620, filed on Nov. 5, 2008.

(51) Int. Cl.
*A61B 5/1455* (2006.01)
*A61B 5/00* (2006.01)

(52) U.S. Cl.
USPC .......................................... 600/324; 600/300

(58) Field of Classification Search
USPC ................ 600/300, 310, 322, 323, 324, 336, 600/481; 340/517, 573.1
See application file for complete search history.

(56) References Cited

U.S. PATENT DOCUMENTS

| | | | |
|---|---|---|---|
| 5,188,108 A | 2/1993 | Secker | |
| 5,285,783 A | 2/1994 | Secker | |
| 5,285,784 A | 2/1994 | Secker | |
| 5,368,026 A | 11/1994 | Swedlow et al. | |
| 5,398,682 A | 3/1995 | Lynn | |
| 5,558,096 A | 9/1996 | Palatnik | |
| 5,584,295 A | 12/1996 | Muller et al. | |
| 5,588,425 A | 12/1996 | Sackner et al. | |
| 5,605,151 A | 2/1997 | Lynn | |
| 5,862,805 A | 1/1999 | Nitzan | |
| 5,865,736 A * | 2/1999 | Baker et al. | 600/323 |
| 5,891,023 A | 4/1999 | Lynn | |
| 6,002,952 A | 12/1999 | Diab et al. | |
| 6,035,223 A | 3/2000 | Baker | |

(Continued)

FOREIGN PATENT DOCUMENTS

| | | |
|---|---|---|
| EP | 0072601 A1 | 2/1983 |
| EP | 1344488 A2 | 9/2004 |

(Continued)

OTHER PUBLICATIONS

Stagg and Gennser, "Electronic analysis of foetal breathing movements: A practical application of phase-locked- loop principles," Journal of Med. Eng. and Tech., Sep. 1978, vol. 2, No. 5, pp. 246-249.

(Continued)

*Primary Examiner* — Eric Winakur

(57) ABSTRACT

Present embodiments are directed to a system and method capable of detecting and graphically indicating physiologic patterns in patient data. For example, present embodiments may include a monitoring system that includes a monitor capable of receiving input relating to patient physiological parameters and providing indications or alarms related to oxygen saturation declines and oxygen desaturation patterns associated with sleep apnea. Present embodiments may include methods and systems for mediating between alarms and other indicators associated with oxygen desaturation and ventilatory instability.

20 Claims, 8 Drawing Sheets

(56) References Cited

U.S. PATENT DOCUMENTS

| | | |
|---|---|---|
| 6,081,742 A | 6/2000 | Amano et al. |
| 6,095,984 A | 8/2000 | Amano et al. |
| 6,129,675 A | 10/2000 | Jay |
| 6,135,966 A | 10/2000 | Ko |
| 6,178,261 B1 | 1/2001 | Williams et al. |
| 6,223,064 B1 | 4/2001 | Lynn |
| 6,229,856 B1 | 5/2001 | Diab et al. |
| 6,238,351 B1 | 5/2001 | Orr et al. |
| 6,325,761 B1 | 12/2001 | Jay |
| 6,334,065 B1 | 12/2001 | Al-Ali et al. |
| 6,342,039 B1 | 1/2002 | Lynn et al. |
| 6,350,242 B1 | 2/2002 | Doten et al. |
| 6,405,076 B1 | 6/2002 | Taylor et al. |
| 6,463,311 B1 | 10/2002 | Diab |
| 6,506,153 B1 | 1/2003 | Littek et al. |
| 6,561,986 B2 | 5/2003 | Baura et al. |
| 6,564,077 B2 | 5/2003 | Mortara |
| 6,606,511 B1 | 8/2003 | Al-Ali et al. |
| 6,609,016 B1 | 8/2003 | Lynn |
| 6,684,090 B2 | 1/2004 | Al-Ali et al. |
| 6,694,178 B1 | 2/2004 | Soula et al. |
| 6,702,752 B2 | 3/2004 | Dekker |
| 6,709,402 B2 | 3/2004 | Dekker |
| 6,748,252 B2 | 6/2004 | Lynn et al. |
| 6,754,516 B2 * | 6/2004 | Mannheimer ............... 600/323 |
| 6,760,608 B2 | 7/2004 | Lynn |
| 6,783,498 B2 | 8/2004 | Sackner et al. |
| 6,816,741 B2 | 11/2004 | Diab |
| 6,839,581 B1 | 1/2005 | El Solh et al. |
| 6,896,661 B2 | 5/2005 | Dekker |
| 6,905,470 B2 | 6/2005 | Lee et al. |
| 6,925,324 B2 | 8/2005 | Shusterman |
| 6,931,269 B2 | 8/2005 | Terry |
| 6,966,878 B2 | 11/2005 | Schoisswohl et al. |
| 6,970,792 B1 | 11/2005 | Diab |
| 6,980,679 B2 | 12/2005 | Jeung et al. |
| 7,020,507 B2 | 3/2006 | Scharf et al. |
| 7,035,679 B2 | 4/2006 | Addison et al. |
| 7,043,293 B1 | 5/2006 | Baura |
| 7,044,918 B2 | 5/2006 | Diab |
| 7,070,566 B2 | 7/2006 | Medero et al. |
| 7,079,888 B2 | 7/2006 | Oung et al. |
| 7,147,601 B2 | 12/2006 | Marks et al. |
| 7,177,682 B2 | 2/2007 | Lovett |
| 7,190,261 B2 | 3/2007 | Al-Ali |
| 7,215,986 B2 | 5/2007 | Diab et al. |
| 7,218,966 B2 | 5/2007 | Haefner |
| 7,254,425 B2 | 8/2007 | Lowery et al. |
| 7,283,870 B2 | 10/2007 | Kaiser et al. |
| 7,336,982 B2 | 2/2008 | Yoo |
| 7,355,512 B1 * | 4/2008 | Al-Ali ............... 600/322 |
| 7,367,339 B2 | 5/2008 | Bickle |
| 7,367,949 B2 | 5/2008 | Korhonen et al. |
| 7,398,115 B2 | 7/2008 | Lynn |
| 7,403,806 B2 | 7/2008 | Norris |
| 7,407,486 B2 | 8/2008 | Huiku et al. |
| 7,415,297 B2 | 8/2008 | Al-Ali et al. |
| 7,438,683 B2 | 10/2008 | Al-Ali et al. |
| 7,440,787 B2 | 10/2008 | Diab |
| 7,470,235 B2 | 12/2008 | Moriya et al. |
| 7,485,095 B2 | 2/2009 | Shusterman |
| 7,496,393 B2 | 2/2009 | Diab et al. |
| 7,499,835 B2 * | 3/2009 | Weber et al. ............... 600/310 |
| 7,523,011 B2 | 4/2009 | Akiyama et al. |
| 7,561,912 B2 | 7/2009 | Schatz et al. |
| 7,610,324 B2 | 10/2009 | Troyansky et al. |
| 7,690,378 B1 | 4/2010 | Turcott |
| 7,801,591 B1 | 9/2010 | Shusterman |
| 7,869,980 B2 | 1/2011 | Casler et al. |
| 7,894,868 B2 | 2/2011 | Al-Ali et al. |
| 7,899,507 B2 | 3/2011 | Al-Ali et al. |
| 7,976,472 B2 | 7/2011 | Kiani |
| 7,988,637 B2 | 8/2011 | Diab |
| 8,019,400 B2 | 9/2011 | Diab et al. |
| 8,046,040 B2 * | 10/2011 | Ali et al. ............... 600/310 |
| 8,130,105 B2 * | 3/2012 | Al-Ali et al. ............... 600/316 |
| 8,203,438 B2 * | 6/2012 | Kiani et al. ............... 600/322 |
| 8,275,553 B2 | 9/2012 | Amundson et al. |
| 8,364,225 B2 | 1/2013 | Diab et al. |
| 2002/0117173 A1 | 8/2002 | Lynn et al. |
| 2003/0036685 A1 | 2/2003 | Goodman |
| 2003/0158466 A1 | 8/2003 | Lynn |
| 2003/0163054 A1 | 8/2003 | Dekker |
| 2004/0015091 A1 | 1/2004 | Greenwald et al. |
| 2005/0004479 A1 | 1/2005 | Townsend et al. |
| 2005/0022606 A1 | 2/2005 | Partin et al. |
| 2005/0027205 A1 | 2/2005 | Tarassenko et al. |
| 2005/0049470 A1 | 3/2005 | Terry |
| 2005/0070774 A1 | 3/2005 | Addison et al. |
| 2005/0222502 A1 | 10/2005 | Cooper |
| 2005/0222503 A1 | 10/2005 | Dunlop et al. |
| 2006/0122476 A1 | 6/2006 | Van Slyke |
| 2006/0192667 A1 | 8/2006 | Al-Ali |
| 2006/0211930 A1 | 9/2006 | Scharf et al. |
| 2006/0217614 A1 | 9/2006 | Takala et al. |
| 2006/0258921 A1 | 11/2006 | Addison et al. |
| 2007/0004977 A1 | 1/2007 | Norris |
| 2007/0010723 A1 | 1/2007 | Uetela et al. |
| 2007/0073120 A1 | 3/2007 | Li et al. |
| 2007/0073124 A1 | 3/2007 | Li et al. |
| 2007/0129636 A1 | 6/2007 | Friedman et al. |
| 2007/0149890 A1 | 6/2007 | Li et al. |
| 2007/0179369 A1 | 8/2007 | Baker |
| 2007/0213619 A1 | 9/2007 | Lindner |
| 2007/0213621 A1 | 9/2007 | Reisfeld et al. |
| 2007/0255146 A1 | 11/2007 | Andrews et al. |
| 2007/0293896 A1 | 12/2007 | Haefner |
| 2008/0077022 A1 | 3/2008 | Baker |
| 2008/0167540 A1 | 7/2008 | Korhonen et al. |
| 2008/0200775 A1 | 8/2008 | Lynn |
| 2009/0247837 A1 | 10/2009 | Ochs et al. |
| 2009/0326349 A1 | 12/2009 | McGonigle |
| 2009/0326395 A1 | 12/2009 | Watson |
| 2009/0326831 A1 | 12/2009 | McGonigle et al. |
| 2010/0113904 A1 | 5/2010 | Batchelder et al. |
| 2010/0113908 A1 | 5/2010 | Vargas et al. |
| 2010/0113909 A1 | 5/2010 | Batchelder et al. |
| 2010/0286495 A1 | 11/2010 | McGonigle |
| 2011/0066062 A1 | 3/2011 | Banet et al. |
| 2011/0071406 A1 | 3/2011 | Addison et al. |

FOREIGN PATENT DOCUMENTS

| | | |
|---|---|---|
| EP | 1507474 B1 | 2/2009 |
| WO | WO 00/21438 | 4/2000 |
| WO | WO 03/000125 A1 | 1/2003 |
| WO | WO 03/055395 A1 | 7/2003 |
| WO | WO 03/084396 A1 | 10/2003 |
| WO | WO 2004/075746 A2 | 9/2004 |
| WO | WO 2010/030238 A1 | 3/2010 |

OTHER PUBLICATIONS

Rapaport and Cousin, "New phase-lock tracking instrument for foetal breathing monitoring," Med. & Biol. Eng. & Comp. 1982, vol. 20, pp. 1-6.

Lindberg, L.G., Ughall, H., Oberg, P.A., "Monitoring of respiratory and heart rates using a fibre-optic sensor," Medical & Biological Engineering & Computing, Sep. 1992, pp. 533-537.

* cited by examiner

SYSTEM AND METHOD FOR FACILITATING OBSERVATION OF MONITORED PHYSIOLOGIC DATA

RELATED APPLICATION

This application claims the benefit of U.S. Provisional Application No. 61/111,620 filed Nov. 5, 2008, which application is hereby incorporated herein by reference.

BACKGROUND

The present disclosure relates generally to user-interface applications for patient monitoring devices. In particular, present embodiments relate to display features that facilitate observation of monitored physiological data with patient monitoring instruments.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Patient monitors include medical devices that facilitate measurement and observation of patient physiological data. For example, pulse oximeters are a type of patient monitor. A typical patient monitor cooperates with a sensor to detect and display a patient's vital signs (e.g., temperature, pulse rate, or respiratory rate) and/or other physiological measurements (e.g., water content of tissue, or blood oxygen level) for observation by a user (e.g., clinician). For example, pulse oximeters are generally utilized with related sensors to detect and monitor a patient's functional oxygen saturation of arterial hemoglobin (i.e., $SpO_2$) and pulse rate. Other types of patient monitors may be utilized to detect and monitor other physiological parameters. The use of patient monitors may improve patient care by facilitating supervision of a patient without continuous attendance by a human observer (e.g., a nurse or physician).

A patient monitor may include a screen that displays information relating to operation and use of the patient monitor. A typical patient monitor screen may display patient data for further interpretation by a user. Such display information may include indications that relate to a patient's physiological conditions. In addition, a patient monitor may also be capable of generating alarms related to the patient's condition (e.g., changes in a physiological parameter), as well as alarms related to certain operating characteristics of the monitor itself (e.g., low battery alarms). These patient-related alarms may alert a caregiver to conditions that may benefit from medical intervention. However, because a monitor may display various patient information that may be associated with a number of alarms, a monitor may generate so many alarms that the patient's rest is disturbed, and the caregiver may not be able to quickly interpret an individual alarm, particularly if multiple alarms are triggered at once.

BRIEF DESCRIPTION OF THE DRAWINGS

Advantages of present embodiments may become apparent upon reading the following detailed description and upon reference to the drawings in which.

DETAILED DESCRIPTION

Figure 1:
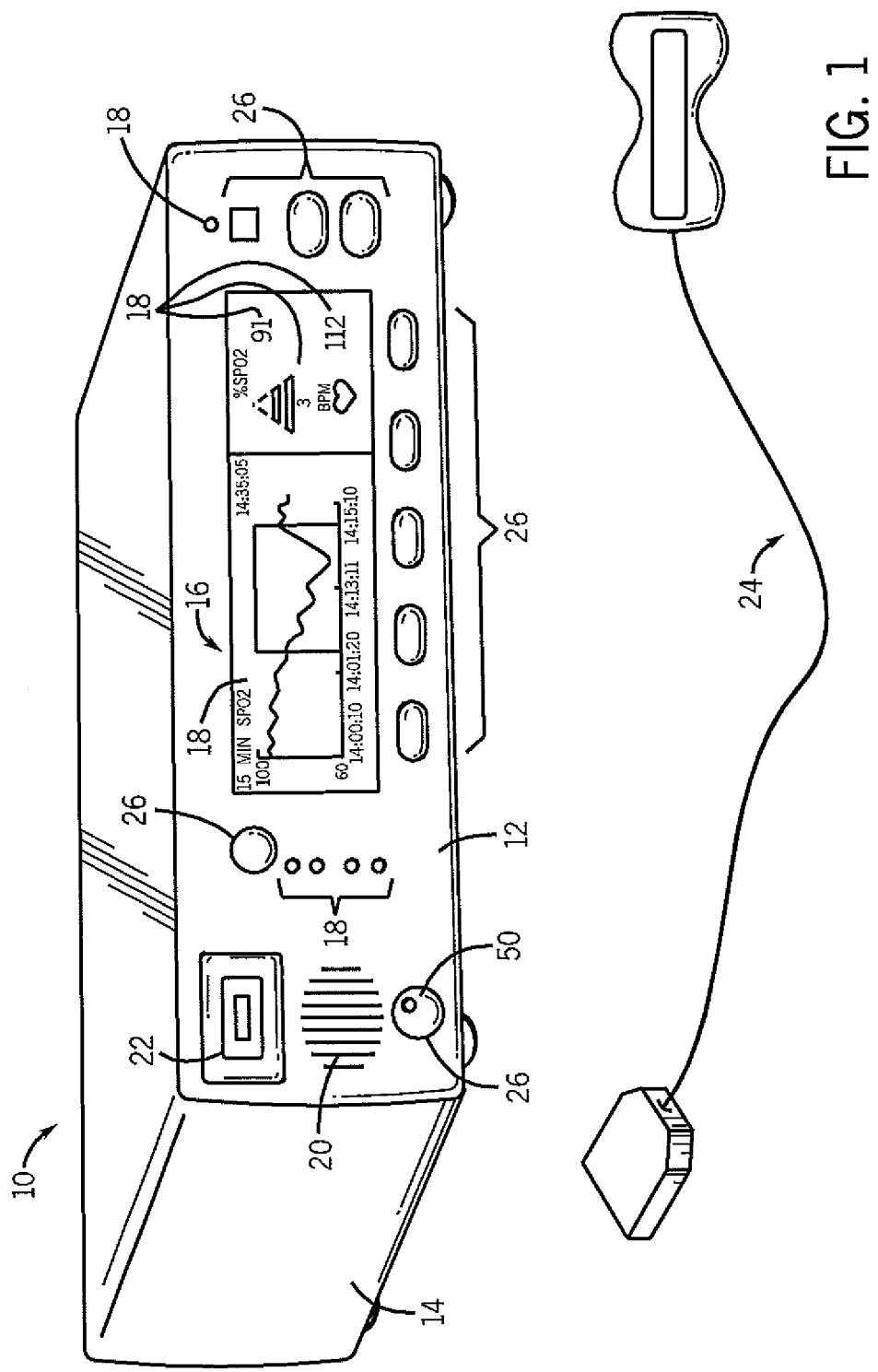
FIG. 1 is a perspective view of an exemplary patient monitor.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments provide methods and systems for mediating between multiple alarms and indicators on a medical device such as a patient monitor. As provided, when an indicator related to a patient parameter, e.g., oxygen saturation, is displayed with or without other related indicators, its alarm settings and/or display characteristics may be altered depending upon which other indicators and alarms are present. For example, to efficiently and effectively utilize alarms, it may be useful to limit alarm settings for metrics that may have overlapping effects. Specifically, certain aspects of sleep apnea monitoring may overlap the monitoring of oxygen saturation declines, and, thus, when both metrics are being monitored, it may be desirable to change the tolerance settings for oxygen saturation alarms to reduce redundant alarms. Accordingly, a monitor in accordance with present embodiments may impose certain tolerance settings for alarms related to a first metric, such has oxygen saturation declines, when alarms related to a second metric, such as sleep apnea detection, are enabled. Because a user, or in certain embodiments a manufacturer, may enable or disable certain monitoring functionalities, for example a sleep apnea monitoring functionality, the present embodiments may provide a medical device with alarm management that mediates alarm settings and tolerance levels to reduce alarm redundancies.

Medical devices, in the course of monitoring a patient, may generate certain alerts that provide information to a caregiver about a patient's physiological condition. For example, a pulse oximetry device may include a graphical indicator or other display alert that notifies a caregiver when a patient's oxygen saturation dips below a certain range or threshold. A caregiver may wish to be alerted to such changes because declines in oxygen saturation may be associated with a range of clinical conditions.

In a patient care environment, a sleeping patient may awaken before a nurse has had the opportunity to acknowledge the alarm, investigate the patient's condition, and/or silence the alarm. To eliminate false alarms that may irritate the patient, the alarm may include certain limits that may reduce alarm notifications for short, sudden dips in oxygen saturation that may be associated with signal interference rather than a change in a patient's condition. For example, an alarm related to oxygen desaturation may only be triggered if an oxygen saturation decline lasts for a certain amount of time or happens with a certain frequency. Such limits may be part of a more complex algorithm or saturation decline detection feature for determining whether a user should be notified of a saturation decline. In addition, the alarm limits may further be determined by user input. For example, a user may decide that an alarm should be more tolerant, and, thus, trigger a notification when the saturation decline is of a greater magnitude lasts for a longer period of time, and/or occurs with a higher frequency. On the other hand, alarm limits that are less tolerant, i.e., more stringent, may trigger a user notification when a relatively smaller decline in oxygen saturation occurs, or when the decline lasts for a relatively shorter duration, and/or occurs with a lower frequency.

In embodiments, a medical device may facilitate observation of a patient's oxygen saturation and may generate alarms associated with both saturation declines and certain patterns associated with saturation declines. For example, certain patterns in oxygen saturation data gathered by a medical monitoring system may be used to assess sleep apnea. Obstructive sleep apnea is a condition in which a patient's breathing is temporarily interrupted when sleeping, and may be assessed by looking for characteristic patterns of ventilatory instability in the oxygen saturation data. These patterns may be detected by the monitor, and appropriate indicators of these patterns may be provided on a display with corresponding alerts and/or alarms.

In embodiments in which a medical monitor may assess both ventilatory instability and saturation declines, it may be advantageous to eliminate or reduce alarms that may be redundant between these two monitoring functions. For example, in certain embodiments, a saturation decline detection feature may trigger an alarm when a certain number of "dips" below threshold occur in a given time period, i.e., an alarm limit may be associated with a certain frequency of desaturation events. Additionally, a ventilatory instability detection feature may also trigger an alarm when a cluster is detected, which may occur when these dips are part of a desaturation pattern. In such an exemplary case, the saturation decline alarm may be redundant, because the ventilatory instability detection feature may monitor such clusters of desaturation. In other words, while the pattern detection feature and the saturation decline detection feature are monitoring different metrics, their monitoring may overlap and, in embodiments, may trigger two different alarms in response to the same oxygen desaturation events. Accordingly, a medical monitor may adjust its alarm settings and tolerance limits for monitoring both saturation declines and ventilatory instability to reduce redundant alarms.

FIG. 1 is a perspective view of a patient monitor 10 in accordance with an exemplary embodiment of the present disclosure. Specifically, the patient monitor 10 illustrated by FIG. 1 is a pulse oximeter that is configured to detect and monitor blood oxygen saturation levels, pulse rate, and so forth. It should be noted that while the illustrated embodiment includes a pulse oximeter, other embodiments may include different types of patient monitors 10. For example, the patient monitor 10 may be representative of a vital signs monitor, a critical care monitor, an obstetrical care monitor, or the like.

The illustrated patient monitor 10 includes a front panel 12 coupled to a body 14 of the monitor 10. The front panel 12 includes a display screen 16 and various indicators 18 (e.g., indicator lights and display screen graphics) that facilitate operation of the monitor 10 and observation of a patient's physiological metrics (e.g., pulse rate). Some of the indicators 18 are specifically provided to facilitate monitoring of a patient's physiological parameters. For example, the indicators 18 may include representations of the most recently measured values for $SpO_2$, pulse rate, index values, and pulse amplitude. In embodiments, the indicators 18 may include an indicator related to ventilatory instability and an indicator related to oxygen saturation declines. In an embodiment, one indicator 18 may be a triangular indicator that is related to an index of ventilatory instability determined by the monitor 10. When the index increases, the triangle fills from bottom to top. In an embodiment, the indicators 18 may also include Sat Seconds indicator that provides an indication related to low oxygen saturation. Other indicators 18 may be specifically provided to facilitate operation of the monitor 10. For example, the indicators 18 may include an A/C power indicator, a low battery indicator, an alarm silence indicator, a mode indicator, and so forth. The front panel 12 may also include a speaker 20 for emitting audible indications (e.g., alarms), a sensor port 22 for coupling with a sensor 24 (e.g., a temperature sensor, a pulse oximeter sensor) and other monitor features.

Additionally, the front panel 12 may include various activation mechanisms 26 (e.g., buttons and switches) to facilitate management and operation of the monitor 10. For example, the front panel 12 may include function keys (e.g., keys with varying functions), a power switch, adjustment buttons, an alarm silence button, and so forth. It should be noted that in other embodiments, the indicators 18 and activation mechanisms 26 may be arranged on different parts of the monitor 10. In other words, the indicators 18 and activation mechanisms 26 need not be located on the front panel 12. Indeed, in some embodiments, activation mechanisms 26 are virtual representations in a display or actual components disposed on separate devices.

Figure 2:
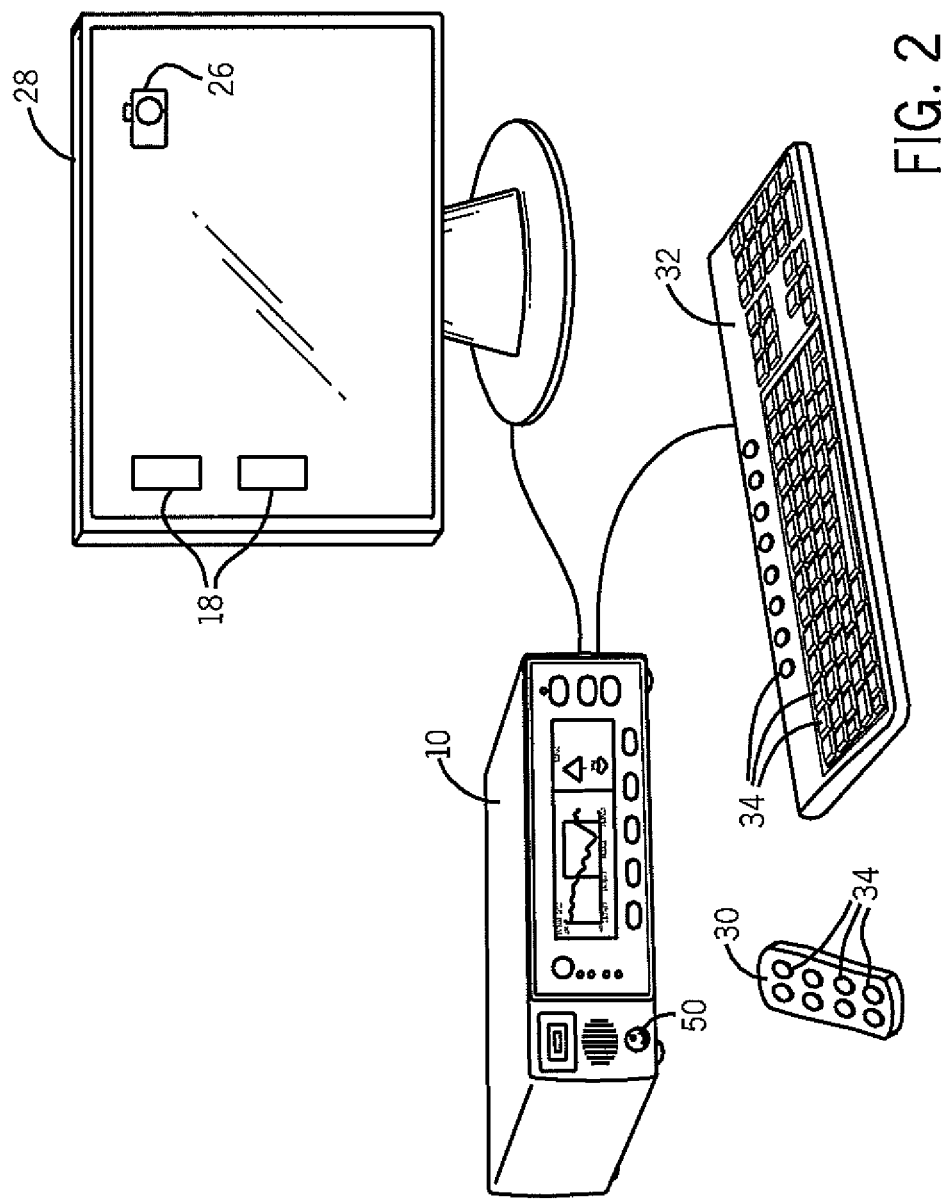
FIG. 2 is a perspective view of the exemplary patient monitor in a system with separate devices.

In some embodiments, as illustrated in FIG. 2, the monitor 10 may cooperate with separate devices, such as a separate screen 28, a wireless remote 30, and/or a keyboard 32. These separate devices may include some of the indicators 18 and activation mechanisms 26 described above. For example, buttons 34 on the remote 30 and/or keyboard 32 may operate as activation mechanisms 26. Specifically, for example, the buttons 34 may cause the monitor 10 to perform specific operations (e.g., power up, adjust a setting, silence an alarm) when actuated on the separate device. Similarly, the indicators 18 and/or activation mechanisms 26 may not be directly disposed on the monitor 10. For example, the indicators 18 may include icons, indicator lights, or graphics on the separate screen 28 (e.g., a computer screen). Further, the activation mechanisms 26 may include programs or graphic features that can be selected and operated via a display. It should be noted that the separate screen 28 and/or the keyboard 32 may communicate directly or wirelessly with the monitor 10.

Figure 3:
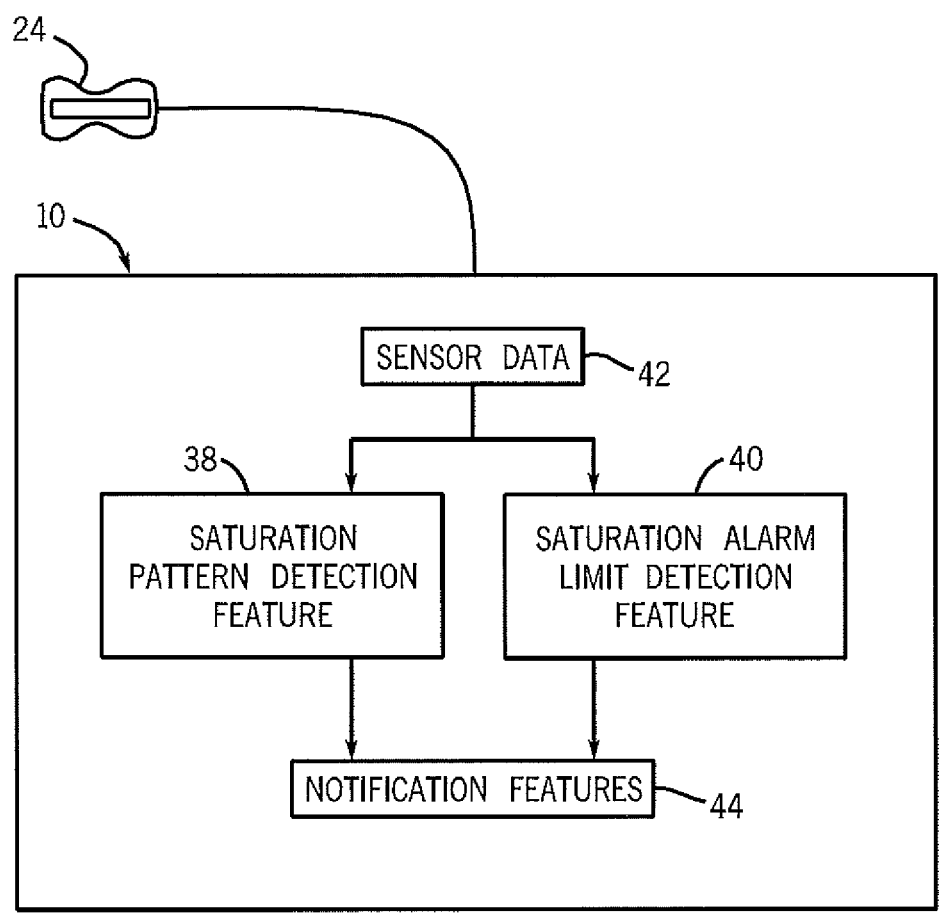
FIG. 3 is a block diagram of an exemplary electronic device.

FIG. 3 shows an exemplary block diagram of a monitor 10 including saturation pattern detection feature 38 and a saturation alarm limit detection feature 40. Data 42 collected by a sensor 24 may be processed by the monitor 10 in any suitable manner and reported to both the saturation pattern detection feature 38 and the saturation alarm limit detection feature 40. The sensor data 24 may be analyzed by one or both of the saturation pattern detection feature 38 and the saturation alarm limit detection feature 40 (both discussed below) to provide an output to one or more notification features 44. The notification features 44 may include an output for display on a display screen 28, such as a graphical or text indicator, an output to drive indicator lights, and/or an output to audible alarm structures, such as speakers.

Figure 4:
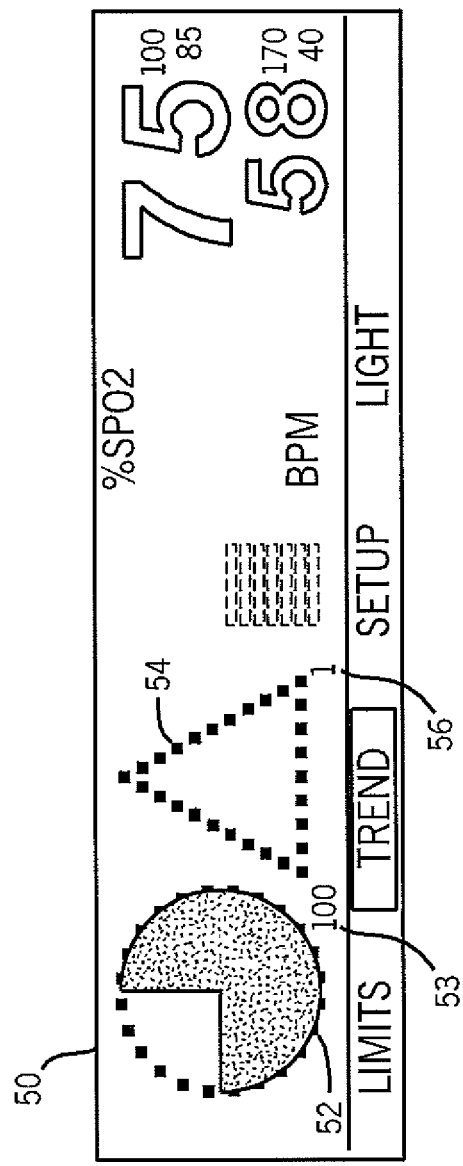
FIG. 4 is a representation of an exemplary display with graphical indicators.

FIG. 4 is an exemplary display 50 including exemplary user notifications of graphical indicators for notifying a healthcare provider about patient ventilatory instability (via saturation pattern detection feature 38) and oxygen desaturation (via saturation alarm limit detection feature 40). In embodiments, a desaturation indicator 52 may be a Sat Seconds indicator that relates to oxygen saturation information. As shown, a SatSeconds indicator may be displayed as a dashed circle that may fill up in relation to the information provided by a calculation algorithm, such as one that may be stored in a memory (e.g., a mass storage device, an EEPROM, an optical memory device, a RAM, a ROM, or any other device for storing machine-readable instructions) and executed by a processor as part of a saturation alarm limit detection feature 40.

Sat Seconds indicator 52 may assist a healthcare provider in focusing on desaturations related to a patient condition rather than short desaturations that may be the result of measurement anomalies. The Sat Seconds indicator 52 may display results determined by the saturation alarm limit detection feature 40 (i.e., a Sat Second analyzing function), which in an embodiment analyzes desaturation events by multiplying their duration (seconds) by the number of percentage points the patient exceeds the alarm limit.

In an embodiment, the saturation alarm limit detection feature 40 may determine if an oxygen desaturation event has occurred by analyzing a plot of oxygen saturation versus time. The Sat Seconds saturation alarm limit detection feature 40 may integrate the area under the curve of time spent below a certain oxygen saturation threshold. Accordingly, sudden, short desaturation readings that may be measurement noise (e.g., that otherwise may trigger nuisance alarms) may be eliminated from a Sat Seconds counter clock while more prolonged desaturations may be counted. In embodiments, a SatSeconds limit, or clock, shown as indicator may be set to 10, 25, 50 or 100 SatSeconds, with 100 SatSecond representing the highest tolerance (i.e. least stringent (and 10 SatSeconds representing the lowest tolerance (i.e., most stringent) settings. In an embodiment, the clock may be set to 100, and therefore only events that equal or surpass the 100 SatSeconds limit may trigger an alarm. In addition, the Sat Seconds indicator 52 may fill up in relation to the Sat Seconds count. For example, the indicator 52 may be full when the count reaches 100. In embodiments, the saturation alarm limit detection feature 40 may incorporate techniques such as those provided in U.S. Pat. No. 5,865,736 to Baker Jr. et al., U.S. Pat. No. 6,754,516 to Mannheimer, and U.S. Pat. No. 7,123,950 to Mannheimer, the specifications of which are incorporated by reference in their entireties herein for all purposes.

In embodiments, the display 50 may also include a Saturation Pattern Detection (SPD) graphical indicator 54 that may provide information to a user related to the occurrence, frequency, and/or magnitude of the patterns detected. The information may be based on a scoring metric, for example a Saturation Pattern Detection index (SPDi index), as provided herein, which is proportional to the magnitude and variability of qualified reciprocations. The SPD calculation feature may be capable of notifying a user of ventilatory instability that corresponds to a certain SPDi index value. In embodiments, when the SPDi is at or above a threshold setting, the user may be notified via a graphical indicator 54.

As illustrated in FIG. 4, the graphical indicator 54 may be represented on display 50 as a dashed triangle that may graphically fill from top to bottom as a monitored and/or calculated value increases. For example, in one embodiment, the graphical indicator 54 may gradually fill as the SPDi index calculated by an SPDi calculation feature increases. Further, the graphical indicator 54 may include a tolerance level indicator 56 that displays an index, for example 1, 2, or 3, for tolerance or sensitivity settings of High, Medium, and Low, respectively, for the SPDi calculation feature. The tolerance settings may set the threshold for triggering a change in the graphical indicator 54 and/or for triggering SPD-associated alarms (e.g., audible and/or visual alarms). As shown in FIG. 4, the graphical indicator 54 may be empty, indicating that an SPDi index is below a certain threshold.

The indicator 54 may have multiple possible display states, which may include: empty, 25% full, 50% full, 75% full, or 100% full. In embodiments, the indicator 54 may fill in any suitable manner. For example, a graphical indicator may have any number of fill states, e.g., filling up in 10%, 20%, 25%, or 50% increments. A filled state of the graphical indicator 54 may trigger a primary or secondary alarm. In an embodiment, a primary alarm, such as a text alert, may be triggered when the graphical indicator 54 begins to fill. When the indicator 54 has reached a full state, a secondary alarm, such as an audio alarm, may then be triggered. The "filling up" may represent the addition of a fill (e.g., any color pixels) to the area of the triangle. In one embodiment, the graphical indicator 54 may fill up when the calculated SPDi index is higher than a tolerance setting. As noted, the High Tolerance, Medium Tolerance, and Low Tolerance alarm limits may refer to certain default values of the SPDi index, such as 24, 15, and 6, respectively. When the SPDi index is higher than, for example, 24 (High Tolerance setting), the graphical indicator 54 may begin to fill. In an embodiment, the graphical indicator 54 may begin to fill up when the SPDi index is lower than but near 24, whereby an SPDi index of 24 represents a "full" state. In such an embodiment, the approximately 25% full graphical indicator as shown may represent an SPDi index of, for example, 18.

Figure 5:
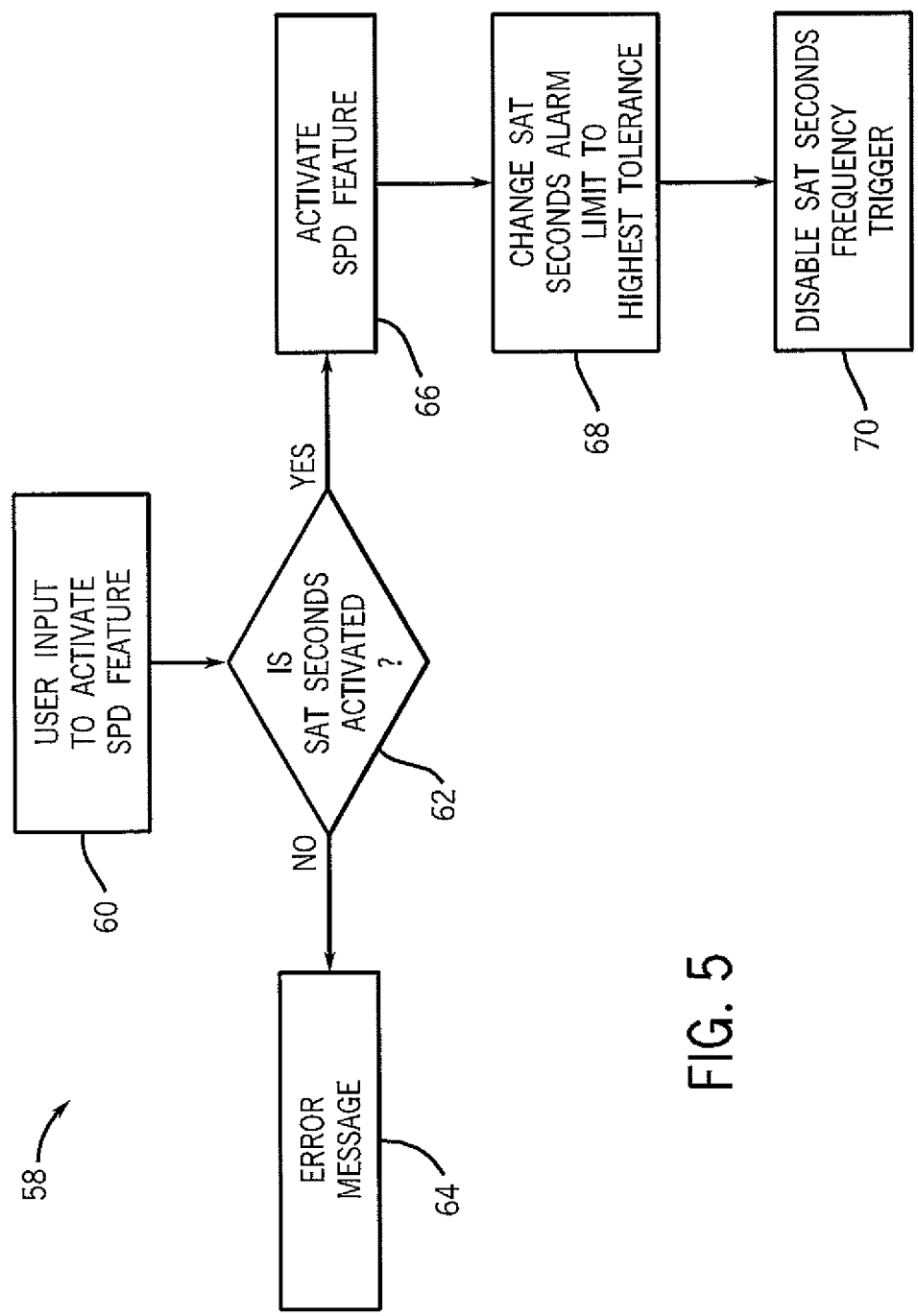
FIG. 5 is an exemplary flowchart depicting a method of mediating between ventilatory instability alarms and saturation alarm limit detection alarms.

In embodiments, a user may have the ability to change certain settings on the monitor 10 related to the graphical indicators and monitoring function. FIG. 5 is a flow chart depicting a method 58 of mediating between SPD monitoring functions and indicators and saturation alarm limits (e.g. Sat Seconds limits) and indicators. In an embodiment, a user may be able to select an option in which the monitor 10 activates SPD calculation features 38 and associated indicators and alarms (step 60).

In embodiments, the SPD feature 38 may be activated only when a Sat Seconds feature, such as saturation alarm limit feature 40, is also active in such embodiments, prior to activating the SPD feature 38, the monitor may establish whether a Sat Seconds calculation and/or display feature is activated at step 62. In embodiments in which Sat Seconds is not active and initiation of the SPD feature 38 is being requested, the monitor 10 may display an error message or other notification at step 64. In embodiments in which Sat Seconds is active, the monitor 10 may activate the SPD feature 38 (step 66) and adjust or mediate the Sat Seconds alarm and notification settings to account for the additional features provided in the SPD feature 38. For example, at step 68, a Sat Seconds alarm limit may be automatically raised to a higher tolerance upon activation of the SPD feature 38. The monitor 10 may assess the setting of the Sat Seconds tolerance, and if the tolerance is not already set to a highest possible level, the monitor 10 may automatically reset the Sat Seconds tolerance. In such an embodiment, with a Sat Seconds alarm limit set to a higher tolerance, alarms associated with oxygen desaturation may occur less frequently while SPD-associated alarms for ventilatory instability may be triggered. Because certain aspects of the SPD calculation feature 38 may overlap with the saturation alarm limit detection feature 40, by setting a Sat Seconds limit to a higher tolerance, redundant alarm triggering may be reduced. In addition, the occurrence of redundant alarms may also be reduced if certain overlapping monitoring features of the saturation alarm limit detection feature 40 calculation or algorithm are disabled. For example, at step 70, a frequency trigger portion of the algorithm may be disabled. For example, a portion of the saturation alarm limit detection feature 40 that triggers a Sat Seconds count when a certain number of oxygen saturation dips occurs within a certain time period, no matter their magnitude or duration, may be disabled. Because the SPD calculation feature 38 may monitor and assess the occurrence of desaturation clusters, it may be redundant to trigger an additional alarm with the saturation alarm limit detection feature 40 when clusters of desaturations occur in a short time period.

In an embodiment, a user may be able to change the default values on the limits to user-selected values and override the Sat Seconds alarm limit. In addition, a user may select between multiple SPD tolerance settings for High, Medium, or Low Tolerance of the SPD-associated alarms. In an embodiment, a monitor 10 may store certain default values associated with SPDi index values. These default values may be determined based on clinical observations of a test patient population or other input from healthcare providers. For example, the default High Tolerance value may be associated with an SPDi index value of 24. Accordingly, any SPD-associated alarms may not trigger until the SPDi index for a calculated window of time is at or near 24.

In another embodiment, a user may input specific values for High, Medium, and Low Tolerance limits. A user may select any value, so long as the High Tolerance limit is higher than the Medium Tolerance limit, and the Medium Tolerance limit is higher than the Low Tolerance limit. A monitor 10 may be able trigger an error message if a user attempts to set a limit of less than zero or if a user attempts to set a High Tolerance limit that is lower than a Medium Tolerance limit, and so on.

Figure 6:
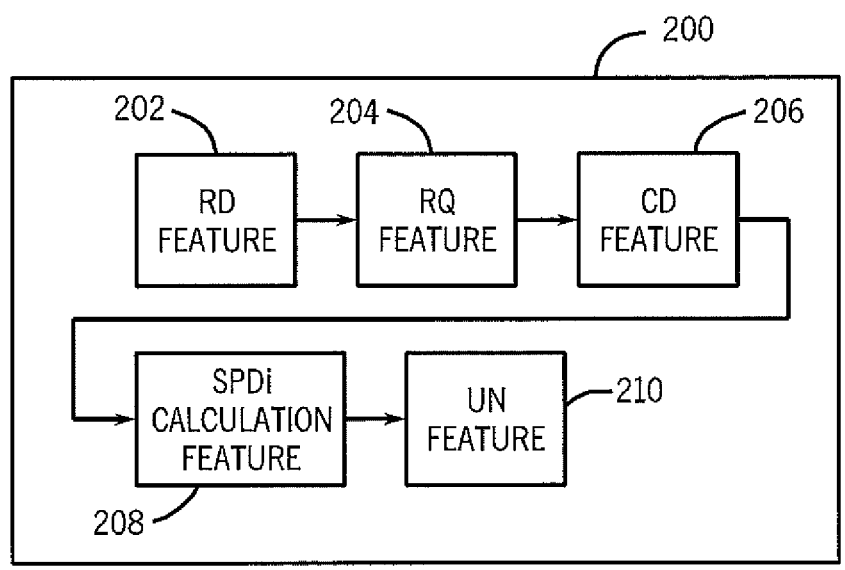
FIG. 6 is a block diagram of an exemplary electronic device.

Monitoring of ventilatory instability that may be associated with sleep apnea may be accomplished via saturation pattern detection feature 38. SPD feature 38 may be stored on a tangible, computer-readable medium (e.g., a memory) and/or hardware capable of detecting the presence of a saturation pattern in a series of physiologic data. For example, FIG. 6 is a block diagram of an electronic device or pattern detection feature 38 in accordance with present embodiments. The electronic device is generally indicated by the reference number 200. The electronic device 200 (e.g., an $SpO_2$ monitor and/or memory device) may comprise various subsystems represented as functional blocks in FIG. 6. Those of ordinary skill in the art will appreciate that the various functional blocks shown in FIG. 6 may comprise hardware elements (e.g., circuitry), software elements (e.g., computer code stored on a hard drive) or a combination of both hardware and software elements. For example, each functional block may represent software code and/or hardware components that are configured to perform portions of an algorithm. Specifically, in the illustrated embodiment, the electronic device 200 includes a reciprocation detection (RD) feature 202, a reciprocation qualification (RQ) feature 204, a cluster determination (CD) feature 206, SPD calculator feature 208, and a user notification (UN) feature 210. Each of these components and the coordination of their functions will be discussed in further detail below.

It should be noted that, in order to detect certain data patterns, embodiments of the present disclosure may utilize systems and methods such as those disclosed in U.S. Pat. Nos. 6,760,608, 6,223,064, 5,398,682, 5,605,151, 6,748,252, U.S. application Ser. No. 11/455,408 filed Jun. 19, 2006, U.S. application Ser. No. 11/369,379 filed Mar. 7, 2006, and U.S. application Ser. No. 11/351,787 filed Feb. 10, 2006. Accordingly, U.S. Pat. Nos. 6,760,608, 6,223,064, 5,398,682, 5,605, 151, 6,748,252, U.S. application Ser. No. 11/455,408 filed Jun. 19, 2006, U.S. application Ser. No. 11/369,379 filed Mar. 7, 2006, and U.S. application Ser. No. 11/351,787 filed Feb. 10, 2006 are each incorporated herein by reference in their entirety for all purposes.

Figure 7:
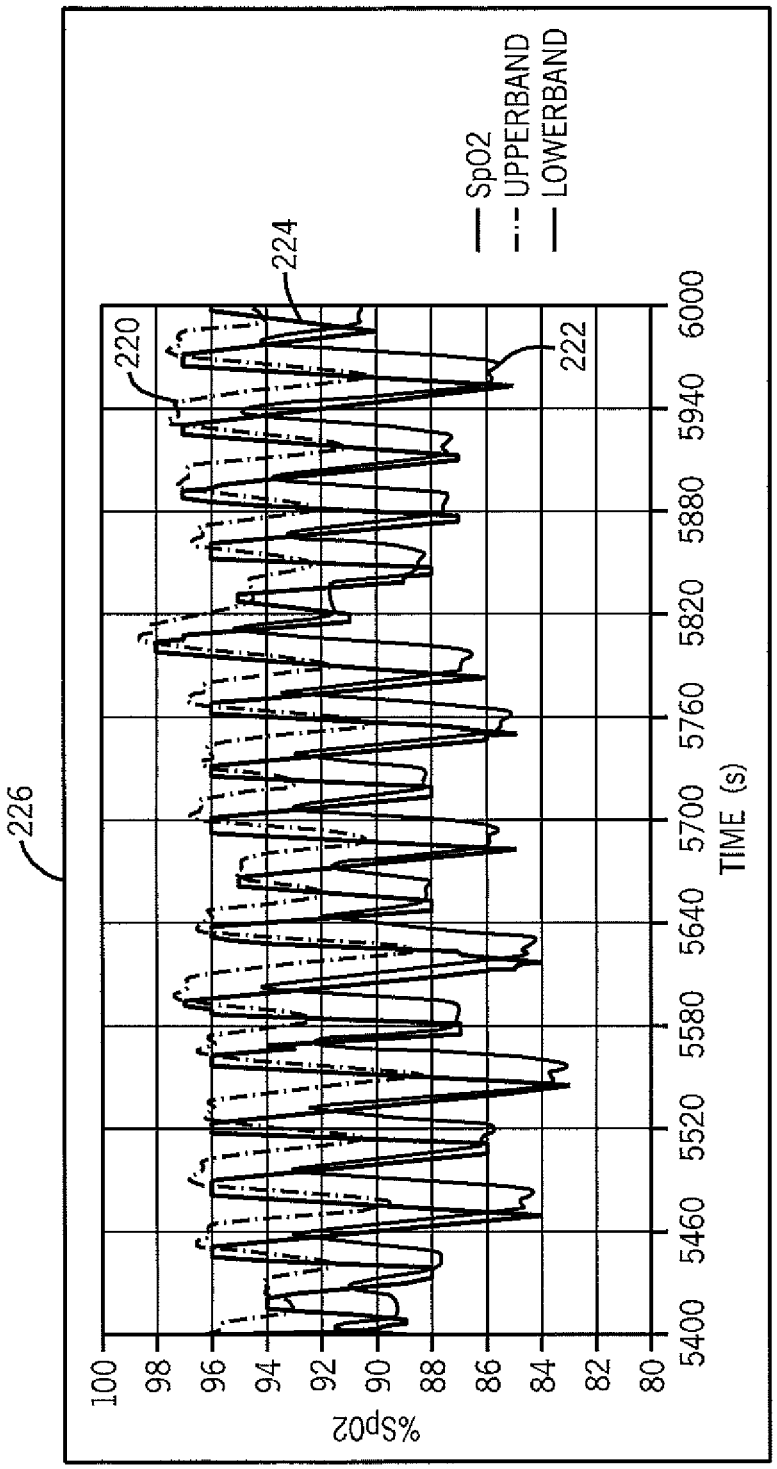
FIG. 7 is an exemplary graph of $SpO_2$ trend data with an upper band and lower band based on mean and standard deviation values.

The RD feature 202 may be capable of performing an algorithm for detecting reciprocations in a data trend. Specifically, the algorithm of the RD feature 202 may perform a statistical method to find potential reciprocation peaks and nadirs in a trend of $SpO_2$ data. A nadir may be defined as a minimum $SpO_2$ value in a reciprocation. The peaks may include a rise peak (e.g., a maximum $SpO_2$ value in a reciprocation that occurs after the nadir) and/or a fall peak (e.g., a maximum $SpO_2$ value in a reciprocation that occurs before the nadir). Once per second, the RD feature 202 may calculate a 12 second rolling mean and standard deviation of the $SpO_2$ trend. Further, based on these mean and standard deviation values, an upper band 220 and lower band 222 with respect to an $SpO_2$ trend 224, as illustrated by the graph 226 in FIG. 7, may be calculated as follows:

Upper Band=mean+standard deviation;

Lower Band=mean−standard deviation.

Once the upper band 220 and lower band 222 have been determined, potential reciprocation peaks and nadirs may be extracted from the $SpO_2$ trend 224 using the upper band 220 and the lower band 224. Indeed, a potential peak may be identified as the highest $SpO_2$ point in a trend segment which is entirely above the upper band 220. Similarly, a potential nadir may be identified as the lowest $SpO_2$ point in a trend segment that is entirely below the lower band 222. In other words, peaks identified by the RD feature 202 may be at least one standard deviation above the rolling mean, and nadirs identified by the RD feature 202 may be at least one standard deviation below the mean. If there is more than one minimum value below the lower band 222, the last (or most recent) trend point may be identified as a nadir. If more than one maximum value is above the upper band 220, the point identified as a peak may depend on where it is in relation to the nadir. For example, regarding potential peaks that occur prior to a nadir (e.g., fall peaks) the most recent maximum trend point may be used. In contrast, for peaks that occur subsequent to a nadir (e.g., rise peaks), the first maximum point may be used. In the example trend data represented in FIG. 7, a peak and nadir is detected approximately every 30-60 seconds.

In one embodiment, a window size for calculating the mean and standard deviation may be set based on historical values (e.g., average duration of a set number of previous reciprocations). For example, in one embodiment, a window size for calculating the mean and standard deviation may be set to the average duration of all qualified reciprocations in the last 6 minutes divided by 2. In another embodiment, an adaptive window method may be utilized wherein the window size may be initially set to 12 seconds and then increased as the length of qualified reciprocations increases. This may be done in anticipation of larger reciprocations because reciprocations that occur next to each other tend to be of similar shape and size. If the window remained at 12 seconds, it could potentially be too short for larger reciprocations and may prematurely detect peaks and nadirs. The following equation or calculation is representative of a window size determination, wherein the output of the filter is inclusively limited to 12-36 seconds, and the equation is executed each time a new reciprocation is qualified:

If no qualified reciprocations in the last 6 minutes:

Window Size=12 (initial value)

else:

RecipDur=½*current qualified recip duration+½*previous RecipDur Window Size=bound(RecipDur, 12,36).

With regard to $SpO_2$ signals that are essentially flat, the dynamic window method may fail to find the three points (i.e., a fall peak, a rise peak, and a nadir) utilized to identify a potential reciprocation. Therefore, the RD feature 202 may limit the amount of time that the dynamic window method can search for a potential reciprocation. For example, if no reciprocations are found in 240 seconds plus the current adaptive window size, the algorithm of the RD feature 202 may timeout and begin to look for potential reciprocations at the current $SpO_2$ trend point and later. The net effect of this may be that the RD feature 202 detects potential reciprocations less than 240 seconds long.

Once potential peaks and nadirs are found using the RD feature 202, the RQ feature 204 may pass the potential reciprocations through one or more qualification stages to determine if a related event is caused by ventilator), instability. A first qualification stage may include checking reciprocation metrics against a set of limits (e.g., predetermined hard limits). A second qualification stage may include a linear qualification function. In accordance with present embodiments, a reciprocation may be required to pass through both stages in order to be qualified.

As an example, in a first qualification stage, which may include a limit-based qualification, four metrics may be calculated for each potential reciprocation and compared to a set of limits. Any reciprocation with a metric that falls outside of these limits may be disqualified. The limits may be based on empirical data. For example, in some embodiments, the limits may be selected by calculating the metrics for potential reciprocations from sleep lab data where ventilatory instability is known to be present, and then comparing the results to metrics from motion and breathe-down studies. The limits may then be refined to filter out true positives.

The metrics referred to above may include fall slope, magnitude, slope ratio, and path length ratio. With regard to fall slope, it may be desirable to limit the maximum fall slope to filter out high frequency artifact in the $SpO_2$ trend, and limit the minimum fall slope to ensure that slow $SpO_2$ changes are not qualified as reciprocations. Regarding magnitude, limits may be placed on the minimum magnitude because of difficulties associated with deciphering the difference between ventilatory instability reciprocations and artifact reciprocations as the reciprocation size decreases, and on the maximum magnitude to avoid false positives associated with sever artifact (e.g., brief changes of more than 35% $SpO_2$ that are unrelated to actual ventilatory instability). The slope ratio may be limited to indirectly limit the rise slope for the same reasons as the fall slope is limited and because ventilatory instability patterns essentially always have a desaturation rate that is slower than the resaturation (or recovery) rate. The path length ratio may be defined as Path Length/((Fall Peak−Nadir)+(Rise Peak−Nadir)), where Path Length=Σ|Current $SpO_2$ Value−Previous $SpO_2$ value' for all $SpO_2$ values in a reciprocation, and the maximum path length ratio may be limited to limit the maximum standard deviation of the reciprocation, which limits high frequency artifact. The following table (Table I) lists the above-identified metrics along with their associated equations and the limits used in accordance with one embodiment:

TABLE I

| Metric | Equation | Minimum | Maximum |
|---|---|---|---|
| Fall Slope | (Nadir − Fall Peak)/Time between Fall Peak and Nadir | −1.6 (Fast Response Mode) −1 (Normal Response Mode) | −0.08 (Fast Response Mode) −0.05 (Normal Response Mode) |
| Magnitude | Max(Rise Peak, Fall Peak) − Nadir | 3 | 35 |
| Slope Ratio | |Fall Slope/Rise Slope| | 0.05 | 1.75 |
| Path Length Ratio | Path Length = Σ|Current SpO2 Value − Previous SpO2 Value| for all SpO2 values in a Reciprocation. Path Length Ratio = Path Length/((Fall Peak − Nadir) + (Rise Peak − Nadir)) | N/A | 2 |

As indicated in Table I above, an oximetry algorithm in accordance with present embodiments may operate in two response modes: Normal Response Mode or Fast Response Mode. The selected setting may change the $SpO_2$ filtering performed by the oximetry algorithm, which in turn can cause changes in $SpO_2$ patterns. Therefore a saturation pattern detection feature may also accept a response mode so that it can account for the different $SpO_2$ filtering. Table I indicates values associated with both types of response mode with regard to the Fall Slope values.

A second qualification stage of the RQ feature 204 may utilize a object reciprocation qualification feature. Specifically, the second qualification stage may utilize a linear qualification function based on ease of implementation, efficiency, and ease of optimization. The equation may be determined by performing a least squares analysis. For example, such an analysis may be performed with MATLAB®. The inputs to the equation may include the set of metrics described below. The output may be optimized to a maximum value for patterns where ventilatory instability is known to be present. The equation may be optimized to output smaller values (e.g., 0) for other data sets where potential false positive reciprocations are abundant.

To simplify optimization, the equation may be factored into manageable sub-equations. For example, the equation may be factored into sub-equation 1, sub-equation D, and sub-equation 2, as will be discussed below. The output of each sub-equation may then be substituted into the qualification function to generate an output. The outputs from each of the sub-equations may not be utilized to determine whether a reciprocation is qualified in accordance with present embodiments. Rather, an output from a full qualification function may be utilized to qualify a reciprocation. It should be noted that the equations set forth in the following paragraphs describe one set of constants. However, separate sets of constants may be used based on the selected response mode. For example, a first set of constants may be used for the Normal Response Mode and a second set of constants may be used for the Fast Response Mode.

Preprocessing may be utilized in accordance with present embodiments to prevent overflow for each part of the qualification function. The tables (Tables II-VII) discussed below, which relate to specific components of the qualification function may demonstrate this overflow prevention. Each row in a table contains the maximum value of term which is equal to the maximum value of the input variable multiplied by the constant, wherein the term "maximum" may refer to the largest possible absolute value of a given input. Each row in a table contains the maximum intermediate sum of the current term and all previous terms. For example, a second row may be noted that in the tables for each sub-equation below, equations may be calculated using temporary signed 32-bit integers, and, thus, for each row in a table where the current term or intermediate term sum exceeds 2147483647 or is less than −2147483647 then an overflow/underflow condition may occur.

A first sub-equation, sub-equation 1, may use metrics from a single reciprocation. For example, sub-equation 1 may be represented as follows:

$$\text{Eq1Score} = \text{SlopeRatio}*\text{SrCf} + \text{PeakDiff}*\text{PdCf} + \text{FallSlope}*\text{FsCf} + \text{PathRatio}*\text{PrCf} + \text{Eq1Offset},$$

where SrCf, PdCf, FsCf, PrCf, and Eq1Offset may be selected using least squares analysis (e.g., using MATLAB®). PeakDiff may be defined as equal to |Recip Fall Peak−Recip Rise Peak|. It should be noted that PeakDiff is typically not considered in isolation but in combination with other metrics to facilitate separation. For example, a true positive reciprocation which meets other criteria but has a high peak difference could be an incomplete recovery. That is, a patient's $SpO_2$ may drop from a baseline to a certain nadir value, but then fail to subsequently recover to the baseline. However, when used in combination with other metrics in the equation, PeakDiff may facilitate separation of two classifications, as large peak differences are more abundant in false positive data sets.

With regard to sub-equation 1, the tables (Tables II and III) set forth below demonstrate that the inputs may be preprocessed to prevent overflow. Further, the tables set forth below include exemplary limits that may be utilized in sub-equation 1 in accordance with present embodiments. It should be noted that Table II includes Fast Response Mode constants and Table III includes Normal Response Mode constants.

TABLE II

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| PeakDiff * PdCf | U8 | 100 | None. This value may not exceed 100 since the maximum $SpO_2$ value accepted is 100 | −29282 | −2928200 | −2928200 | NO |
| SlopeRatio * SrCf | U8 | 255 | None | −1534 | −391170 | −3319370 | NO |
| FallSlope * FsCf | S16 | −32768 | None | −19 | 622592 | −2696778 | NO |
| PathRatio * PrCf | U16 | 65535 | None | −7982 | −523100370 | −525797148 | NO |
| Eq1Offset | N/A | N/A | N/A | 809250 | 809250 | −524987898 | NO |

TABLE III

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| PeakDiff * PdCf | U8 | 100 | None. This value may not exceed 100 since the maximum SpO2 value accepted is 100 | −33311 | −3331100 | −3331100 | NO |
| SlopeRatio * SrCf | U8 | 255 | None | −2151 | −548505 | −3879605 | NO |
| FallSlope * FsCf | S16 | −32768 | None | −706 | 23134208 | 19254603 | NO |
| PathRatio * PrCf | U16 | 65535 | None | −6178 | −404875230 | −385620627 | NO |
| Eq1Offset | N/A | N/A | N/A | 576330 | 576330 | −385044297 | NO | contain the maximum output for the second term calculated, as well as the maximum sum of terms 1 and 2. It should be noted that the order of the row may match the order that the terms are calculated by the RQ feature 204. Further, it should A second sub-equation, sub-equation D, may correspond to a difference between two consecutive reciprocations which have passed the hard limit qualifications checks, wherein consecutive reciprocations include two reciprocations that are separated by less than a defined time span. For example, consecutive reciprocations may be defined as two reciprocations that are less than 120 seconds apart. The concept behind sub-equation D may be that ventilatory instability tends to be a relatively consistent event, with little change from one reciprocation to the next. Artifact generally has a different signature and tends to be more random with greater variation among reciprocations. For example, the following equation may represent sub-equation D:

$$EqD = SlopeRatioDiff*SrDCf + DurationDiff*DDCf + NadirDiff*NdCf + PathLengthRatioDiff*PrDCf\_EqDOffset,$$

where, SrDCf, DDCf, NdCf, PrDCf, and EqDOffset may be selected using least squares analysis (e.g., using MATLAB®). With regard to other variables in sub-equation D, SlopeRatioDiff may be defined as |Current Recip Slope Ratio−Slope Ratio of last qualified Recip|; DurationDiff may be defined as |Current Recip Duration−Duration of last qualified Recip|; NadirDiff may be defined as |Current Recip Nadir−Nadir value of last qualified Recip|; and PathLengthRatioDiff may be defined as |Current Recip Path Length Ratio|Path Length Ratio of last qualified Recip|.

With regard to sub-equation D, the tables (Tables IV and V) set forth below demonstrate that the inputs may be preprocessed to prevent overflow. Further, the tables set forth below include exemplary limits that may be utilized in sub-equation D in accordance with present embodiments. It should be noted that Table IV includes Fast Response Mode constants and Table V includes Normal Response Mode constants.

TABLE IV

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| EqDOffset | N/A | N/A | N/A | 885030 | 885030 | 885030 | NO |
| SlopeRatioDiff * SrDCf | U8 | 255 | None | −2809 | −716295 | 168735 | NO |
| DurationDiff * DDCf | U16 | 240 | The Recip detection module may only detect recips less than or equal to 240 seconds long | −2960 | −710400 | −541665 | NO |
| NadirDiff * NdCf | U8 | 100 | This value may not exceed 100 since the maximum SpO2 value accepted is 100 | −13237 | −1323700 | −1865365 | NO |
| PathLengthRatioDiff * PrDCf | U16 | 65535 | None | −7809 | −511762815 | −513628180 | NO |

TABLE V

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| EqDOffset | N/A | N/A | N/A | 847650 | 847650 | 847650 | NO |
| SlopeRatioDiff * SrDCf | U8 | 255 | None | −2629 | −670395 | 177255 | NO |
| DurationDiff * DDCf | U16 | 240 | The Recip detection module may only detect recips less than or equal to 240 seconds long | −4282 | −1027680 | −850425 | NO |
| NadirDiff * NdCf | U8 | 100 | This value may not exceed 100 since the maximum SpO2 value accepted is 100 | −11705 | −1170500 | −2020925 | NO |
| PathLengthRatioDiff * PrDCf | U16 | 65535 | None | −7844 | −514056540 | −516077465 | NO |

A third sub-equation, sub-equation 2, may combine the output of sub-equation D with the output of sub-equation 1 for a reciprocation (e.g., a current reciprocation) and a previous reciprocation. For example, the following equation may represent sub-equation 2:

Eq2Score=EqDScore*DCf+
    Eq1ScoreCurrent*CurrEq1Cf+
    Eq1ScorePrev*PrevEq1Cf, where DCf, N1Cf, PrevEq1Cf, and Eq2Offset may be selected using least squares analysis (e.g., using MAT-LAB®). With regard to other variables in sub-equation 2, EqDScore may be described as the output of sub-equation D; Eq1ScoreCurrent may be described as the output of sub-equation 1 for a current reciprocation; and Eq1ScorePrev may be described as the output of sub-equation 1 for the reciprocation previous to the current reciprocation.

With regard to sub-equation 2, the tables (Tables VI and VII) set forth below demonstrate that the inputs may be pre-processed to prevent overflow. Further, the tables set forth below include exemplary limits that may be utilized in sub-equation 2 in accordance with present embodiments. It should be noted that Table VI includes Fast Response Mode constants and Table VII includes Normal Response Mode constants.

TABLE VI

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| Eq2Offset | N/A | N/A | N/A | −203800 | −203800 | −203800 | NO |
| EqDScore * Dcf | S32 | −501590 | The largest output for sub-equation D may be −513628180 (see Table IV). The input value may be scaled by dividing the value by 1024. Therefore the largest input value may be −501590 | 529 | −265341110 | −265544910 | NO |
| Eq1ScorePrev * PrevEq1Cf | S32 | −512683 | The largest output for sub-equation 1 may be −524987898 (see Table II). The input value may be scaled by dividing the value by 1024. Therefore the largest input value may be −512683 | 333 | −170723439 | −436268349 | NO |
| Eq1ScoreCurrent * CurrEq1Cf | S32 | −512683 | Same as previous row | 617 | −316325411 | −752593760 | NO |

TABLE VII

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| Eq2Offset | N/A | N/A | N/A | −194550 | −194550 | −194550 | NO |
| EqDScore * DCf | S32 | −503981 | The largest output for sub-equation D may be −516077465 (see Table V). The input value may be scaled by dividing the value by 1024. Therefore the largest input value may be −503981 | 532 | −268117892 | −268312442 | NO |
| Eq1ScorePrev * PrevEq1Cf | S32 | −376000 | The largest output for sub-equation 1 may be −385024297 (see Table III). The input value may be scaled by dividing the value by 1024. Therefore the | 496 | −186496000 | −454808442 | NO |

TABLE VII-continued

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| Eq1ScoreCurrent * CurrEq1Cf | S32 | −376000 | largest input value may be −376000 Same as previous row | 406 | −152656000 | −607464442 | NO |

A qualification function may utilize the output of each of the equations discussed above (i.e., sub-equation 1, sub-equation D, and sub-equation 2) to facilitate qualification and/or rejection of a potential reciprocation. For example, the output of the qualification function may be filtered with an ER filter, and the filtered output of the qualification function may be used to qualify or reject a reciprocation. An equation for an unfiltered qualification function output in accordance with present embodiments is set forth below:

QFUnfiltered=Eq1Score*SingleRecipWt*Eq2Cf+
N2Score*MultipleRecipWt*Eq2Cf+
NConsecRecip*ConsecCf+RecipMax*MaxCf+
Artifact %*ArtCf+QFOffset, where Eq2Cf, ConsecCf, MaxCf, ArtCf, and QFOffset may be selected using least squares analysis (e.g., using MAT-LAB®), and, as indicated above, Eq1 Score may be defined as the output of sub-equation 1.

Other metrics in the unfiltered qualification function include SingleRecipWt, MultipleRecipWt, NConsecRecip, RecipMax, and Artifact %. With regard to SingleRecipWt and MultipleRecipWt, when there are two or more consecutive qualified reciprocations (e.g., qualified reciprocations that are less than 120 seconds apart) present, SingleRecipWt may equal 0 and MultipleRecipWt may equal 1. However, when only a single reciprocation is present, SingleRecipWt may equal 1 and MultipleRecipWt may equal 0.

NConseRecip, which may be defined as equal to max (NConsecRecip',QFConsecMax), may include a count of the number of consecutive reciprocations (e.g., reciprocations that are less than or equal to 120 seconds apart) that have passed the hard limit checks. The value for NConsecRecip may be reset to 0 whenever a gap between any two partially qualified reciprocations exceeds 120 seconds. This may be based on the fact that ventilatory instability is a relatively long lasting event as compared to artifact. Therefore, as more reciprocations pass the hard limit checks, the qualification function may begin qualifying reciprocations that were previously considered marginal. However, to guard against a situation where something is causing a longer term artifact event (e.g., interference from nearby equipment), the value may be clipped to a maximum value to limit the metrics influence on the qualification function output.

RecipMax, which may be defined as equal to max(Fall Peak, Rise Peak), may facilitate making decisions about marginal reciprocations. Indeed, marginal reciprocations with higher maximum $SpO_2$ values may be more likely to get qualified than marginal reciprocations with lower $SpO_2$ values. It should be noted that this metric works in tandem with the NConsecRecip metric, and multiple marginal reciprocations with lower maximum $SpO_2$ values may eventually, over a long period of time, get qualified due to the NConsecRecip metric.

The metric Artifact % may be defined as an artifact percentage that is equal to 100*Total Artifact Count/Recip Duration, where Total Artifact Count is the number of times and artifact flag was set during the reciprocation. Present embodiments may include many metrics and equations that are used to set the artifact flag. Because of this it is a generally reliable indication of the amount of artifact present in the oximetry system as a whole. Marginal reciprocations with a high Artifact % are less likely to be qualified than marginal reciprocations with a low (or 0) artifact percentage.

A last component of the qualification function may include an infinite impulse response (RR) filter that includes coefficients that may be tuned manually using a tool (e.g., a spreadsheet) that models algorithm performance. The filtered qualification function may be represented by the following equation, which includes different constants for different modes (e.g., Fast Response Mode and Normal Response Mode):

QFFiltered=SingleRecipWt*QFUnfiltered+((1−a)
*QFUnfiltered+a*PrevQFFiltered)*MultipleRe-
cipWt, where QFUnfiltered may be defined as the current unfiltered qualification function output; PrevQFFiltered may be defined as the previous filtered qualification function output; and where the constat "a" may be set to 0.34 for Fast Response Mode and 0.5 for Normal Response Mode.

The filtered output of the qualification function may be compared to a threshold to determine if the current reciprocation is the result of RAF or artifact. The optimum threshold may theoretically be 0.5. However, an implemented threshold may be set slightly lower to bias the output of the qualification function towards qualifying more reciprocations, which may result in additional qualification of false positives. The threshold may be lowered because, in accordance with present embodiments, a cluster determination portion of the algorithm, such as may be performed by the CD feature 206, may require a certain number (e.g., 5) of fully qualified reciprocations before an index may be calculated, and a certain number (e.g., at least 2) of consecutive qualified reciprocations (with no intervening disqualified reciprocations) within the set of fully qualified reciprocations. Since multiple reciprocations may be required, the clustering detection method may be biased toward filtering out false positives. Accordingly, the reciprocation qualification function threshold may be lowered to balance the two processes.

The CD feature 206 may be capable of performing an algorithm that maintains an internal reciprocation counter that keeps track of a number of qualified reciprocations that are currently present. When the reciprocation counter is greater than or equal to a certain value, such as 5, the clustering state may be set to "active" and the algorithm may begin calculating and reporting the SPDi. When clustering is not active (e.g., reciprocation count<5) the algorithm may not calculate the SPDi. The SPDi may be defined as a scoring metric associated with the identification of a saturation trend pattern generated in accordance with present embodiment and may correlate to ventilatory instability in a population of sleep lab patients.

The CD feature 206 may utilize various rules to determine the reciprocation count. For example, when the clustering state is inactive, the following rules may be observed:

1.) If the distance between qualified reciprocation exceeds 120 seconds, then the reciprocation count=0;
2.) If the current reciprocation is qualified, and the time from the start of the current reciprocation to the end of the last qualified reciprocation is <=120 seconds, then the reciprocation count=reciprocation count+1;
3.) If the current reciprocation is not qualified, then the reciprocation count=max(reciprocation count−2, 0).

Once clustering is active, it may remain active until the time between two qualified reciprocations exceeds 120 seconds. The following table (Table II) illustrates an example of how the reciprocation count rules may be applied to determine a clustering state.

TABLE VIII

| Current Reciprocation Qualified | Time Since Last Qualified Reciprocation (seconds) | Reciprocation Count | Clustering State |
|---|---|---|---|
| TRUE | N/A | 1 | INACTIVE |
| FALSE | 60 | 0 | INACTIVE |
| TRUE | N/A | 1 | INACTIVE |
| FALSE | 60 | 0 | INACTIVE |
| TRUE | N/A | 1 | INACTIVE |
| TRUE | 30 | 2 | INACTIVE |
| TRUE | 120 | 3 | INACTIVE |
| FALSE | 60 | 1 | INACTIVE |
| TRUE | 10 | 2 | INACTIVE |
| TRUE | 20 | 3 | INACTIVE |
| TRUE | 40 | 4 | INACTIVE |
| FALSE | 30 | 2 | INACTIVE |
| FALSE | 60 | 0 | INACTIVE |
| TRUE | N/A | 1 | INACTIVE |
| TRUE | 20 | 2 | INACTIVE |
| TRUE | 120 | 3 | INACTIVE |
| TRUE | 10 | 4 | INACTIVE |
| FALSE | 90 | 2 | INACTIVE |
| TRUE | 120 | 3 | INACTIVE |
| TRUE | 60 | 4 | INACTIVE |
| TRUE | 20 | 5 | ACTIVE |
| TRUE | 30 | 6 | ACTIVE |
| FALSE | 50 | 6 | ACTIVE |
| FALSE | 100 | 6 | ACTIVE |
| TRUE | 121 | 1 | INACTIVE |
| FALSE | 50 | 0 | INACTIVE |
| TRUE | N/A | 1 | INACTIVE |
| TRUE | 30 | 2 | INACTIVE |
| TRUE | 121 | 1 | INACTIVE |
| TRUE | 10 | 2 | INACTIVE |
| TRUE | 20 | 3 | INACTIVE |
| TRUE | 40 | 4 | INACTIVE |
| TRUE | 40 | 5 | ACTIVE |

When the clustering state is active, the SPDi calculation feature 208 may calculate an unfiltered SPDi for each new qualified reciprocation. The following formula may be used by the SPDi calculation feature 208:

$$\text{Unfiltered SPDi} = a*\text{Magnitude} + b*\text{PeakDelta} + c*\text{NadirDelta};$$

wherein a=1.4, b=2.0, c=0.2;
wherein Magnitude=average magnitude of all reciprocations in the last 6 minutes;
wherein PeakDelta=average of the three highest qualified reciprocation rise peaks in the last 6 minutes minus the average of the three lowest qualified reciprocation rise peaks in the last 6 minutes; and
wherein NadirDelta=average of the three highest qualified reciprocation nadirs in the last 6 minutes minus the average of the three lowest qualified reciprocation nadirs in the last 6 minutes.

Wherein SPDi <=31

The above formula may be utilized to quantify the severity of a ventilatory instability pattern. The constants and metrics used may be based on input from clinical team members. It should be noted that the PeakDelta parameter may be assigned the largest weighting constant since the most severe patterns generally have peak reciprocation values that do not recover to the same baseline.

The unfiltered SPDi may be updated whenever clustering is active and a new qualified reciprocation is detected. Non-zero SPDi values may be latched for a period of time (e.g., 6 minutes). The unfiltered SPDi may then be low pass filtered to produce the final output SPDi value. The following IIR filter with a response time of approximately 40 seconds may be used:

$$\text{SPDi} = \text{Unfiltered SPDi}/a + \text{Previous Filtered SPDi}*(a-1)/a;$$

wherein a=40.

Figure 8:
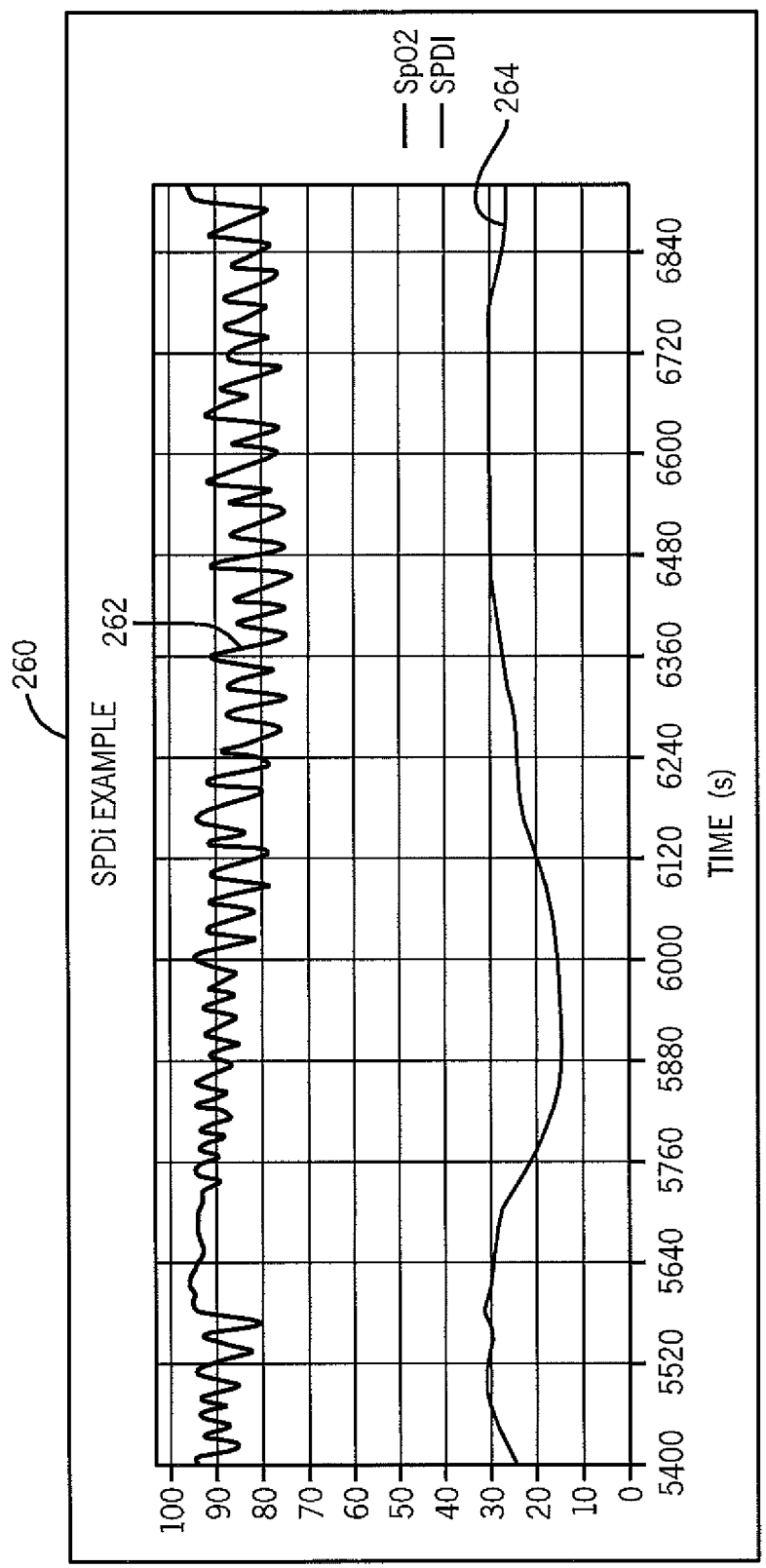
FIG. 8 is an exemplary graph including an $SpO_2$ trend that contains a ventilatory instability $SpO_2$ pattern and a trend of the resulting saturation pattern detection index.

FIG. 8 is an exemplary graph 260 including an $SpO_2$ trend 262 that contains a ventilatory instability $SpO_2$ pattern and a trend of the resulting SPDi 264. In the illustrated example, it should be noted that the SPDi is sensitive to the decreasing peaks (incomplete recoveries) starting at approximately t=6000.

The UN feature 210 may be capable of determining if a user notification function should be employed to notify a user (e.g., via a graphical or audible indicator) of the presence of a detected patterns such as ventilatory instability. The determination of the UN feature 210 may be based on a user configurable tolerance setting and the current value of the SPDi. For example, the user may have four choices for the sensitivity or tolerance setting: Off, Low, Medium, and High. When the sensitivity or tolerance setting is set to Off, an alarm based on detection of a saturation pattern may never be reported to the user. The other three tolerance settings (i.e., Low, Medium, and High) may each map to an SPDi threshold value. For example, Low may map to an SPDi threshold of 6, Medium may map to an SPDi threshold of 15, and High may map to an SPDi threshold of 24. The thresholds may be based on input from users. When the SPDi is at or above the threshold for a given tolerance setting, the user may be notified that ventilatory instability is present. As discussed below, the indication to the user may include a graphical designation of the trend data corresponding to the detected pattern. For example, the trend data utilized to identify a ventilatory instability pattern may be highlighted, flashing, or otherwise indicated on a user interface of a monitor in accordance with present embodiments. Similarly, parameters such as the SPDi value and the tolerance settings may be graphically presented on a display.

While the embodiments of the present disclosure may be susceptible to various modifications and alternative forms, specific embodiments have been shown by way of example in the drawings and will be described in detail herein. However, it should be understood that the present embodiments are not intended to be limited to the particular forms disclosed. Rather, present embodiments are to cover all modifications, equivalents and alternatives falling within the spirit and scope of present embodiments as defined by the following appended claims.

What is claimed is:

1. A method of evaluating a condition of a patient, the method comprising:
   receiving data from a sensor related to one or more physiological parameters of the patient;
   receiving instructions for activating a pattern monitoring function;
   determining, in response to the instructions for activating the pattern monitoring function, a presence of patterns in the data indicative of ventilatory instability and triggering a ventilatory instability alarm based on the presence of the patterns; and
   increasing an alarm tolerance of a desaturation monitoring function when the pattern monitoring function is activated and if the tolerance is below a certain default value, wherein the desaturation monitoring function is capable of analyzing the data and triggering a desaturation alarm based on one or more of a magnitude, frequency, or duration of an oxygen desaturation.

2. The method of claim 1, comprising displaying a first graphical indicator comprising a graphical representation based at least in part on the pattern indicative of ventilatory instability and a second graphical indicator comprising a graphical representation based at least in part on the oxygen desaturation.

3. The method of claim 1, comprising determining a scoring metric associated with the patterns indicative of ventilatory instability.

4. The method of claim 3, wherein triggering the ventilatory instability alarm comprises triggering the ventilatory instability alarm when the scoring metric reaches a predetermined threshold.

5. The method of claim 4, comprising receiving input to set the predetermined threshold.

6. The method of claim 4, wherein the predetermined threshold comprises a high tolerance threshold, a medium tolerance threshold, or a low tolerance threshold.

7. The method of claim 1, comprising determining a scoring metric associated with one or more of the magnitude, frequency, or duration of the oxygen desaturation.

8. The method of claim 7, wherein determining the scoring metric comprises calculating an integral of oxygen desaturation over a period of time.

9. The method of claim 7, wherein triggering the desaturation alarm comprises triggering the desaturation alarm when the scoring metric reaches a predetermined threshold.

10. The method of claim 9, comprising receiving input to set the predetermined threshold.

11. The method of claim 9, wherein the predetermined threshold comprises a high tolerance threshold, a medium tolerance threshold, or a low tolerance threshold.

12. The method of claim 9, wherein increasing the alarm tolerance comprises increasing the predetermined threshold to a highest possible tolerance.

13. The method of claim 7, wherein increasing the alarm tolerance comprises decreasing or eliminating an effect of the frequency of the oxygen desaturation on the scoring metric.

14. A medical device, comprising:
   a microprocessor; and
   a memory storing machine-readable instructions, wherein the contents of the memory comprises machine-readable instructions capable of directing the microprocessor to:
      receive data from a sensor related to one or more physiological parameters of the patient;
      receive instructions for activating a pattern monitoring function, wherein the pattern monitoring function is capable of determining a presence of patterns in the data indicative of ventilatory instability and triggering a ventilatory instability alarm based on the presence of the patterns; and
      increase an alarm tolerance of a desaturation monitoring function when the pattern monitoring function is activated and if the tolerance is below a certain default value, wherein the desaturation monitoring function is capable of analyzing the data and triggering a desaturation alarm based on one or more of a magnitude, frequency, or duration of an oxygen desaturation.

15. The medical device of claim 14, comprising a network interface unit configured to send a signal related to the desaturation alarm or the ventilatory instability alarm to a device located on a local area network.

16. The medical device of claim 14, wherein the desaturation monitoring function is capable of determining a value of an integral of the oxygen desaturation over a period of time by accumulating a product of time and a difference between the oxygen desaturation data and a threshold value.

17. The medical device of claim 14, wherein determining a presence of patterns in the data indicative of ventilatory instability comprises determining the presence of one or more clusters.

18. The medical device of claim 14, comprising a display, and wherein the device is capable of displaying a first graphical indicator comprising a graphical representation based at least in part on the pattern indicative of ventilatory instability and a second graphical indicator comprising a graphical representation based at least in part on the oxygen desaturation.

19. A system, comprising:
   a sensor capable of sensing patient physiological parameters;
   a monitor capable of receiving data from the sensor related to the patient physiological parameters and storing the data related to the parameters, the monitor comprising:
      a pattern detection feature capable of analyzing the data to detect a pattern in the data indicative of ventilatory instability and triggering a ventilatory instability alarm based on the presence of the pattern; and
      a desaturation detection feature capable of analyzing the data and triggering a desaturation alarm based on one or more of a magnitude, frequency, or duration of an oxygen desaturation, wherein when the pattern detection feature is activated, the desaturation alarm is configured to automatically increase an alarm tolerance of the desaturation alarm if the tolerance is below a certain default value.

20. The system of claim 19, wherein the sensor comprises a pulse oximetry sensor.

* * * * *